United States Patent
Schvekher

(10) Patent No.: US 9,483,527 B2
(45) Date of Patent: Nov. 1, 2016

(54) SYSTEM AND METHOD FOR DECISION REASONING

(71) Applicant: Tony Theodor Schvekher, Modiin (IL)

(72) Inventor: Tony Theodor Schvekher, Modiin (IL)

( * ) Notice: Subject to any disclaimer, the term of this patent is extended or adjusted under 35 U.S.C. 154(b) by 200 days.

(21) Appl. No.: 14/071,553

(22) Filed: Nov. 4, 2013

(65) Prior Publication Data

US 2014/0143197 A1 May 22, 2014

Related U.S. Application Data

(60) Provisional application No. 61/729,379, filed on Nov. 22, 2012.

(51) Int. Cl.
| | |
|---|---|
| *G06N 5/00* | (2006.01) |
| *G06F 1/00* | (2006.01) |
| *G06F 17/30* | (2006.01) |
| *G06F 19/00* | (2011.01) |
| *G06Q 10/06* | (2012.01) |

(52) U.S. Cl.
CPC ....... *G06F 17/30483* (2013.01); *G06F 19/345* (2013.01); *G06Q 10/06* (2013.01)

(58) Field of Classification Search
CPC .......... G06N 5/04; G06N 5/02; G06N 5/022; G06N 7/005
See application file for complete search history.

(56) References Cited

U.S. PATENT DOCUMENTS

| | | | |
|---|---|---|---|
| 2003/0061231 A1* | 3/2003 | Lovegren | G06Q 10/10 |
| 2013/0278492 A1* | 10/2013 | Stolarz | G06F 3/01 345/156 |

* cited by examiner

*Primary Examiner* — Stanley K Hill
*Assistant Examiner* — Kalpana Bharadwaj
(74) *Attorney, Agent, or Firm* — Lewis Roca Rothgerber Christie LLP

(57) ABSTRACT

A method for decision reasoning, the method comprising using at least one hardware processor to: provide a database comprising decisions, questions and reasons; receive, from a user, a selection of a decision being part of said decisions; retrieve, from said database, relevant questions out of said questions, wherein said relevant questions are associated, within said database, with said decision received from the user; receive, from the user, answers to at least some of said relevant questions; process said answers so as to retrieve, from said database, one or more relevant reasons out of said reasons; and display said one or more relevant reasons to the user.

14 Claims, 5 Drawing Sheets

So, you've decided to buy a new car, well, well ...

Now I will need some answers from you
Please make them as accurate as possible
A "help-me-help-you" sort of thing. Got it?

OK. Let's start ...

What is your gender?

What is your age?

Where do you live?

Marital status

Kids?

| Question | Yes | No |
|---|---|---|
| Do you spend much time on the road? | ○ | ○ |
| Did your car ever just die on you? | ○ | ○ |
| Do you live far from your work? | ○ | ○ |
| Can potential customers actually see your car? | ○ | ○ |
| Do you spend much on gas? | ○ | ○ |
| Do you enjoy driving? | ○ | ○ |
| Do you work? | ○ | ○ |
| Are you serious about this? | ○ | ○ |
| Do you spend much on repairs and maintenance? | ○ | ○ |
| Are you planning to keep the new car for long, or replace it within 2-3 years? | ○ | ○ |
| Are you happily married or similarly engaged? | ○ | ○ |

Now tell me why this was such a great idea

Fig. 3

Well, here's what I've managed to come up with so far ...

○ It will save me money on gasoline, as newer vehicles are more efficient
○ It will add to my free time
○ I could spend more time with my family and friends
○ It will impress potential customers, as a car represents a certain image statements (Prestige)
○ A new car is more reliable (due to improved technology). It will save me time & money, currently wasted on repairs
○ A new car will last longer Please give us your feedback by choosing the reasons that were helpful and click [here]

Fig. 4

SYSTEM AND METHOD FOR DECISION REASONING

CROSS-REFERENCE TO RELATED APPLICATION(S)4

This application claims priority to and the benefit of U.S. Provisional Application No. 61/729,379, filed Nov. 22, 2012, the entire contents of which are incorporated herein by reference.

FIELD OF THE INVENTION

The invention relates to a system and method for decision reasoning.

BACKGROUND

Decision Support Systems (DSS) are a class of information processing systems that aim at supporting humans with making decisions when solving complicated problems. They are applied in many fields, including medical diagnostics, integrated circuit design, business, finance and more. DSSs are typically designed to provide users with near real-time access to complex bodies of knowledge. Often, the users of DSSs are themselves experts in the bodies of knowledge at which the DSS is targeted, and these users harness the DSS to better apply their knowledge to a particular set of facts. Thus, conventional DSSs accept a set of facts and, based on these facts and the content of the pertinent body of knowledge, provide potential conclusions drawn from application of the pertinent body of knowledge.

There are several ways to classify DSS applications. Not every DSS fits neatly into one of the categories, but may be a mix of two or more architectures. Holsapple and Whinston (1996) classify DSS into the following six frameworks: Text-oriented DSS, Database-oriented DSS, Spreadsheet-oriented DSS, Solver-oriented DSS, Rule-oriented DSS, and Compound DSS. See Holsapple, C.W., and A. B. Whinston. (1996). Decision Support Systems: A Knowledge-Based Approach. St. Paul: West Publishing.

DSSs are commonly designed with a bottom-up approach, in which data such as facts, assumptions and/or factors are input into the system, which processes them vis-à-vis its database and outputs a suggested decision.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, a method for decision reasoning, the method comprising using at least one hardware processor to: provide a database comprising decisions, questions and reasons; receive, from a user, a selection of a decision being part of said decisions; retrieve, from said database, relevant questions out of said questions, wherein said relevant questions are associated, within said database, with said decision received from the user; receive, from the user, answers to at least some of said relevant questions; process said answers so as to retrieve, from said database, one or more relevant reasons out of said reasons; and display said one or more relevant reasons to the user.

There is further provided, in accordance with an embodiment, a non-transitory computer-readable medium having computer-readable code for decision reasoning stored thereon, that, when executed by at least one hardware processor of a computer, causes the computer to: provide a database comprising decisions, questions and reasons; receive, from a user, a selection of a decision being part of said decisions; retrieve, from said database, relevant questions out of said questions, wherein said relevant questions are associated, within said database, with said decision received from the user; receive, from the user, answers to at least some of said relevant questions; process said answers so as to retrieve, from said database, one or more relevant reasons out of said reasons; and display said one or more relevant reasons to the user.

In some embodiments, each of said decisions, questions and reasons is stored in a separate table in said database.

In some embodiments, each of said decisions is structured based at least on a verb, an adjective and a noun.

In some embodiments, each of said questions is of a type selected from the group consisting of a multiple-choice question, a yes/no question and an open-ended question.

In some embodiments, the method further comprises using said at least one hardware processor to: receive from the user feedback as to said one or more relevant reasons; and process said feedback so as to adjust an association in said database between at least one of said one or more relevant reasons and said decision selected by the user.

In some embodiments, the method further comprises using said at least one hardware processor to receive a suggestion of one or more new decisions from the user, and store said one or more new decisions in the database.

In some embodiments, the method further comprises using said at least one hardware processor to receive a suggestion of one or more new reasons from the user, and store said one or more new reasons in the database.

In some embodiments, said computer-readable code, when executed by said at least one hardware processor of the computer, further causes the computer to: receive from the user feedback as to said one or more relevant reasons; and process said feedback so as to adjust an association in said database between at least one of said one or more relevant reasons and said decision selected by the user.

In some embodiments, said computer-readable code, when executed by said at least one hardware processor of the computer, further causes the computer to receive a suggestion of one or more new decisions from the user, and store said one or more new decisions in the database.

In some embodiments, said computer-readable code, when executed by said at least one hardware processor of the computer, further causes the computer to receive a suggestion of one or more new reasons from the user, and store said one or more new reasons in the database.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is

FIG. 3 shows another screenshot of an exemplary implementation of the system;

FIG. 4 shows a further screenshot of an exemplary implementation of the system.

DETAILED DESCRIPTION

Figure 1:
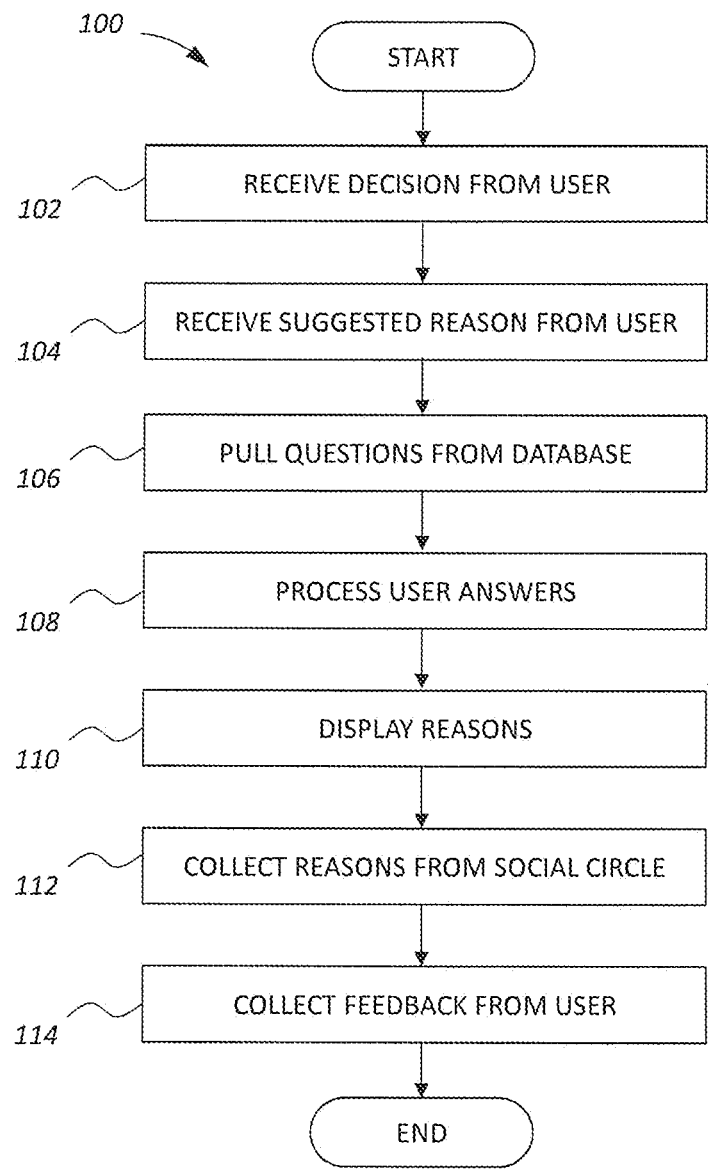
FIG. 1 shows a flow chart of a computer-based method of operating a system for reasoning a decision.

Computer-based system and method for decision reasoning are disclosed herein. The present system and method take an unorthodox, top-down approach, in which a user's decision serves as input, and the processing yields a set of arguments useful for reasoning, and ultimately justifying, the decision. Conventional DSSs, in contrast, are built quite the opposite way, as discussed in the background section above.

Advantageously, the present system and method are capable of providing ex post rationalization to human decisions which were reached based on emotions, heuristics or even a hunch. The rationalization may serve to reassure the person about the correctness of his or her decision, and/or to justify the decision in front of third parties.

Furthermore, the system and method may serve as a tool allowing users to resolve concerns and dilemmas by combining automatic reason generation, as discussed above, with social network integration which seeks advice and/or reasoning from a user's social circle. Today's social networks, such as Facebook and Twitter, allows integration and access to their resources via suitable APIs (application program interfaces). In some embodiments thereof, the system and method integrate with one or more such social networks, to seek the crowd's advice and/or reasoning as to various problems and/or decisions raised by users of the system. Not only can this social network integration provide assistance to a user on an ad-hoc basis, it can also be used to enhance and enlarge the system's database for future uses.

In some embodiments thereof, the system and method include, for example, three entities: decisions, questions and reasons. These (and optionally other) entities may reside in one or more suitable computerized databases, for examples as associated tables. The "decisions" entity includes a list of decisions from which a user may choose. For example, "buy a new car", "invest in U.S. treasury bills", or "get married". Each such "decision" is associated with one or more "question" entities, whose purpose is to gather information from the user, based on which the rationalization is generated. Lastly, the "reasons" entity lists multiple potential reasons (also referred to herein as "justifications") for reaching various decisions; one or more suitable reasons, as determined by the system, are provided to the user based on his or her answers to the questions. Each "decision" may further be associated with multiple ones of the "reasons"; upon receipt of a user's answers to the "questions", the system narrows down the list of "reasons" associated with the pertinent "decision", based on the user's answers.

Advantageously, in some embodiments, machine learning is utilized in order to continuously improve the system and method. For example, feedback may be collected from users after they are presented with reasons for their decisions. Reasons indicated as satisfactory by the users may then be promoted when the system attempts to reason future decisions of the same or a similar type; in contrast, reasons indicated as unsatisfactory may be demoted or even eliminated from future relevant reasoning.

Similar machine learning may be applied on the "questions" entity. User feedback may be gathered, to evaluate the level of relevancy of certain questions to the decisions and/or to the reasons. Additionally or alternatively, the system may automatically analyze the aforementioned relevancy, for example by demoting or eliminating questions which are answered differently by distinct users but still lead to the same or similar reasons. For this purpose, the system may conduct statistical analysis of the activity (decisions, questions, answers and/or reasons) of a vast number of users, thereby gaining insight as to the relevancy of certain questions to the decisions and/or to the reasons.

As another way to improve the reasoning yielded by the system, a user may be requested to complete a demographic questionnaire, which includes details such as age, gender, place of residence, income, education, occupation and/or the like. The system may then tailor the reasons to the specific demographics of a user. Another option is to tailor the questions to specific demographics. Either option may be realized by way of pre-programming of the system, and/or by way of machine learning. A demographic questionnaire may be embedded as part of the questions displayed to the user before generating the reasons. Alternatively, a user's answers to a demographic questionnaire may be saved in the system, and used in subsequent sessions initiated by the same user.

The system, in its pre-use stage, may include initial database records. As mentioned above, the database may include, for example, three main tables, namely—"decisions", "questions" and "reasons", as well as other tables as necessary. The "decisions" table may either include a list of complete decisions, such as "buy a new car", or a multi-dimensional array of words/phrases which may be combined into a meaningful sentence. As an example, the "buy a new car" decision may be structured from three building blocks: verbs (for example "buy", "sell", "get"), adjectives (for example "new", "better", "fast") and nouns ("car", "job", "patent"). Usage of such building blocks to construct decisions may enhance database performance by saving disk space, as there is no need to represent each and every complete decision as a database entry. It may further improve data retrieval times.

The database may further include associations between records of the different tables, so as to link each decision with suitable reasons, and link these reasons with questions that lead to them.

Reference is now made to FIG. 1, which shows a flow chart of a computer-based method 100 of operating a system for reasoning a decision. Steps in the flow chart are not necessarily carried out in order. In a step 102, a user selects a decision, for example by combining a verb, an adjective and a noun, and the system receives the input decision. In one option, the user can choose only decisions (or verb-adjective-noun) combinations that exist in the database. In a second option, the user may input free text as the decision, and the system interprets the text using an NLP (natural language processing) engine.

In a step 104, the user may suggest a reason for this decision. The suggested reasons may be sent to an administrator to consider if it should be added to the database and be associated with that particular decision for future use.

In a step 106, the system pulls, from the database, questions suitable for the decision entered by the user in step 102. Such questions may include, for example, multiple-choice questions, yes/no questions and/or open-ended questions, to which natural language processing (NLP) may be applied, for interpretation purposes. Optionally, some of the questions may be of demographic nature.

In a step 108, the system processes the user's answers to the questions, and pulls, from the database, one or more reasons which are deemed suitable for the user's decision.

In a step 110, the one or more reasons which were deemed suitable are displayed to the user. Optionally, if multiple reasons are displayed, they are ordered according to a "score" determined during the processing of step 108. For example, reasons having a higher score, meaning—they are more relevant, will appear before those reasons with a lower score. This score may be recalculated in subsequent uses of the system, according to user feedback.

Optionally, in a step 112, the user may choose to consult with one or more members of his social circle (hereinafter "friends"), by allowing the system to contact them on his or her behalf via integration with one or more social networks, such as Facebook, Twitter and the like. Each of these friends is then presented with an invitation, either a private one or one published on a friend's public profile (sometimes referred to as "wall"), containing a link to a suitable location in the system. There, the friend can provide reasons and/or other insight relating to the originating user's decision, which are then saved in the system's database—both for presentation to the originating user, and for retention for use in future cases involving the same or a similar decision.

The user may then, in a step 114, provide feedback by selecting those reasons which appeal to him or her the most. The feedback may include, additionally or alternatively, suggestion of new reasons which are applicable, in the user's opinion, to the decision at issue. Optionally, step 114 may further include collection of feedback from the friends referred to in step 112 above. Feedback entered may be structured and/or unstructured. In case the feedback is unstructured, namely—in the form of free text, the system may interpret the text using an NLP engine.

Some embodiments, such as the method and system discussed in relation to FIG. 1, may be implemented using a non-transitory computer-readable medium or article which may store an instruction or a set of instructions that, if executed by a computer (for example, by a hardware processor and/or by other suitable machines), cause the computer to perform a method and/or operations in accordance with embodiments of the invention. Such a computer may include, for example, any suitable processing platform, computing platform, computing device, processing device, computing system, processing system, computer, processor, or the like, and may be implemented using any suitable combination of hardware and/or software. The computer-readable medium or article may include, for example, any type of disk including optical disks, DVD-ROMs, magnetic-optical disks, read-only memories (ROMs), random access memories (RAMs), electrically programmable read-only memories (EPROMs), electrically erasable and programmable read only memories (EEPROMs), magnetic or optical cards, or any other type of media suitable for storing electronic instructions, and capable of being coupled to a computer system bus.

The instructions may include any suitable type of code, for example, source code, compiled code, interpreted code, executable code, static code, dynamic code, or the like, and may be implemented using any suitable high-level, low-level, object-oriented, visual, compiled and/or interpreted programming language, such as C, C++, C#, Java, Fortran, Cobol, assembly language, machine code, or the like.

Exemplary Implementation

In an exemplary implementation, the present system and method have been realized using the PHP programming language, a PostgreSQL database management system (DBMS) and an Apache web server. The PostegreSQL DBMS, specifically, is a state-of-the-art system suitable for big-data scenarios. It has won the "Best Open Source Database" award in the Linux New Media. Awards 2012.

Figure 2:
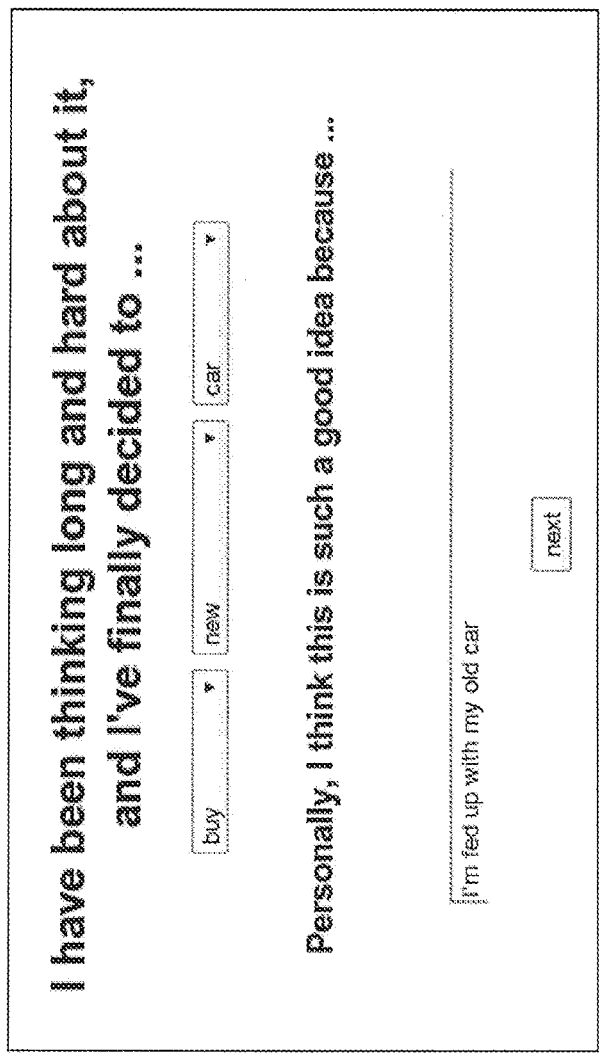
FIG. 2 shows a screenshot of an exemplary implementation of the system.

The exemplary implementation adopted a web service approach, in which the interaction with users is done through a web application server, which users may access through their web browser. Reference is now made to FIGS. 2, 3 and 4, which show screenshots of three stages, respectively, of operating the exemplary implementation of the system. In the first stage, in FIG. 2, the user is prompted to enter his or her decision by structuring a decision from three building blocks: verbs ("buy"), adjectives ("new") and nouns ("car"). Each building block may be selected, for example, from a drop-down menu. The user may also enter some initial reasoning for his or her decision.

In the second stage, shown in FIG. 3, the system pulls, from a database, questions suitable for the decision entered by the user. Such questions may include, for example, multiple-choice questions, yes/no questions and/or open-ended questions (not shown). Optionally, some of the questions may be of demographic nature.

In the third stage, shown in FIG. 4, one or more reasons for the decision are displayed to the user, following a processing step. The user may provide feedback by selecting reasons that appeal to him or her the most.

Figure 5:
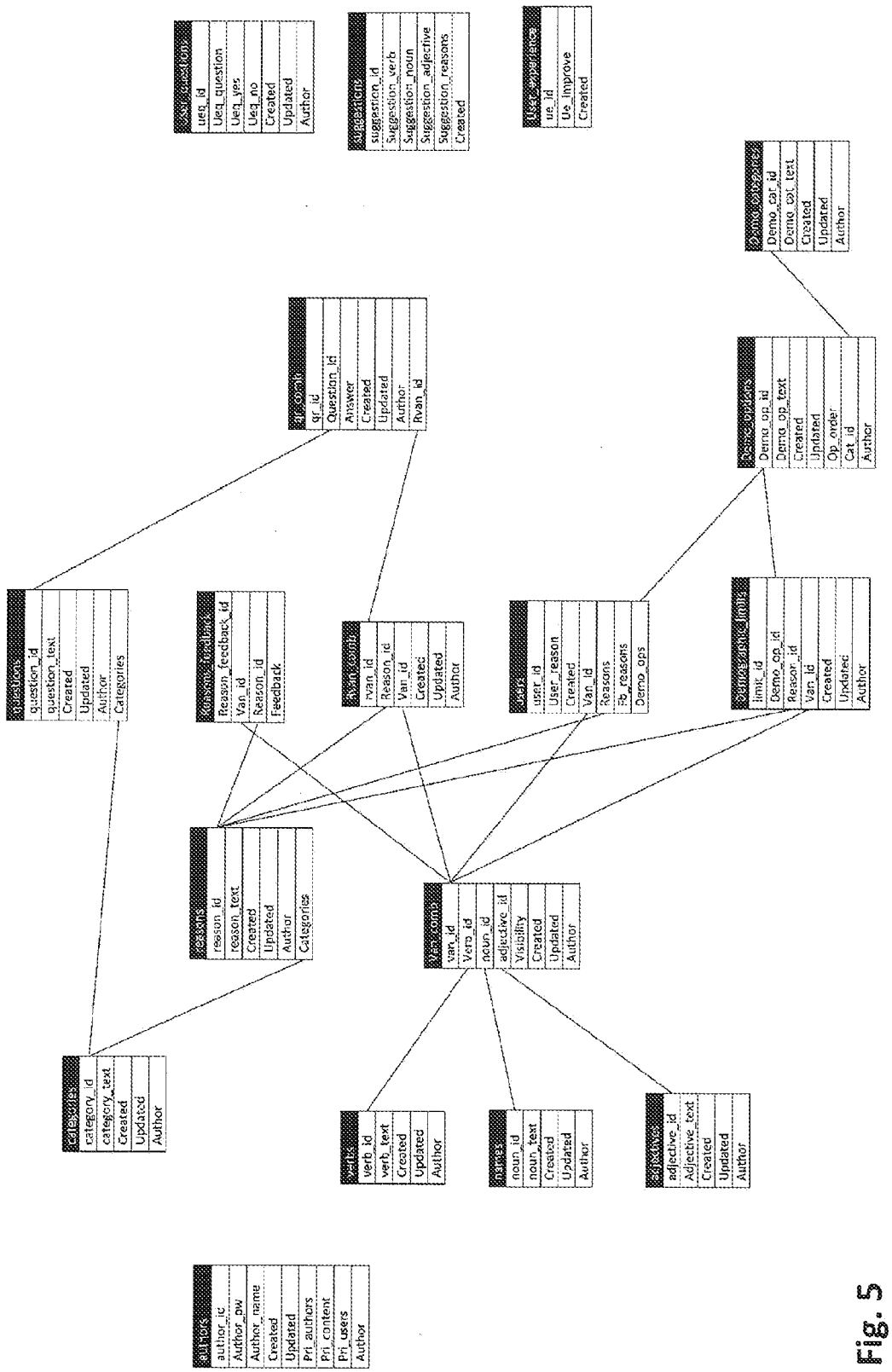
FIG. 5 shows an entity-relationship diagram (ERD) of a database of the exemplary implementation of the system.

Reference is now made to FIG. 5, which shows an entity-relationship diagram (ERD) of a database of the exemplary implementation of the system. The ERD shows the tables of the database and their associations. The following is a description of the tables:

Adjectives

| NAME | TYPE | COMMENTS |
|---|---|---|
| adjective_id | Integer | sequence |
| Adjective_text | Character varying(100) | |
| Created | Timestamp with time zone | |
| Updated | Timestamp with time zone | |
| Author | integer | |

Authors

Administrators' name, password and privileges.

| NAME | TYPE | COMMENTS |
|---|---|---|
| author_id | Integer | sequence |
| Author_pw | Character varying(50) | |
| Author_name | Character varying(20) | |
| Created | Timestamp with time zone | |
| Updated | Timestamp with time zone | |
| Pri_authors | Boolean | Does the author have privileges to change authors' privileges? |

-continued

| NAME | TYPE | COMMENTS |
| --- | --- | --- |
| Pri_content | Boolean | Does the author have privileges to change content? |
| Pri_users | boolean | Does the author have privilege to change data entered by users? |
| Author | integer | |

Categories

Each question or reason can be related to these categories to enable filtering the questions and reasons.

| NAME | TYPE | COMMENTS |
| --- | --- | --- |
| category_id | Integer | sequence |
| category_text | Character varying(100) | |
| Created | Timestamp with time zone | |
| Updated | Timestamp with time zone | |
| Author | integer | |

Demo_categories

Shows the demographic questions that will be presented to the user.

| NAME | TYPE | COMMENTS |
| --- | --- | --- |
| Demo_cat_id | Integer | sequence |
| Demo_cat_text | Character varying(100) | |
| Created | Timestamp with time zone | |
| Updated | Timestamp with time zone | |
| Author | integer | |

Demo_options

All the options that are shown for each demographic question.

| | | |
| --- | --- | --- |
| Demo_op_id | Integer | sequence |
| Demo_op_text | Character varying(100) | |
| Created | Timestamp with time zone | |
| Updated | Timestamp with time zone | |
| Op_order | Integer | |
| Cat_id | Integer | Holds the demo_cat_id from demo_categories that this options relates to. |
| Author | integer | |

Demographic_limits

This table contains all the demographic limits for the combination of reason and verb-adjective-noun association. If a user checked a demographic option that is limited in this combination, the reason would not be shown for that user.

| | | |
| --- | --- | --- |
| limit_id | Integer | sequence |
| Demo_op_id | Character varying(100) | Holds the demo_op_id from the demo_options table |
| Reason_id | Integer | Holds the reason_id from reasons table |
| Van_id | Integer | Holds the van_id from van_comb table |
| Created | Timestamp with time zone | |
| Updated | Timestamp with time zone | |
| Author | integer | |

Nouns

| NAME | TYPE | COMMENTS |
| --- | --- | --- |
| noun_id | Integer | sequence |
| noun_text | Character varying(100) | |
| Created | Timestamp with time zone | |
| Updated | Timestamp with time zone | |
| Author | integer | |

Qr_comb

This table contains all the relations between questions and instances of combining a reason to a verb-adjective-noun association. Each combination has one or more questions and the reason is suggested to the user according to the answers the user gives to the questions under this combination. When a user answers are different from the ones that appear in this table, the reason is not suggested to the user. (Reasons can be combined with a verb-adjective-noun association more than once, so even though one instance of this reason will be removed from the list of suggestions, it might still be shown to the user if the user answers the matching answers for another instance).

| NAME | TYPE | COMMENTS |
| --- | --- | --- |
| qr_id | Integer | sequence |
| Question_id | Integer | Holds the question_id from the questions table |
| Answer | Boolean | |
| Created | Timestamp with time zone | |
| Updated | Timestamp with time zone | |
| Author | integer | |
| Rvan_id | Integer | Holds the rvan_id from rvan_comb |

Questions

| NAME | TYPE | COMMENTS |
| --- | --- | --- |
| question_id | Integer | sequence |
| question_text | Character varying(100) | |
| Created | Timestamp with time zone | |
| Updated | Timestamp with time zone | |
| Author | integer | |
| Categories | Integer[ ] | Array of all related category_ids from categories table |

Reasons

| NAME | TYPE | COMMENTS |
|---|---|---|
| reason_id | Integer | sequence |
| reason_text | Character varying(100) | |
| Created | Timestamp with time zone | |
| Updated | Timestamp with time zone | |
| Author | integer | |
| Categories | Integer[ ] | Array of all related category_ids from categories table |

Reasons_feedback

This table keeps counting the positive feedbacks reasons get when suggested to an association of verb-adjective-noun. This table is used to order the reasons that are suggested to a user.

| NAME | TYPE | COMMENTS |
|---|---|---|
| Reason feedback_id | Integer | sequence |
| Van_id | Integer | Holds the van_id from van_comb table |
| Reason_id | Integer | Holds reason_id from reasons table |
| Feedback | Integer | A counter that increment every time a user checks this reason as useful when suggested as a reason for this verb-adjective-noun association |

Rvan_comb

This table shows all instances of combining a reason to a verb-adjective-noun association.

| NAME | TYPE | COMMENTS |
|---|---|---|
| rvan_id | Integer | sequence |
| Reason_id | Integer | Reason_id from reasons table |
| Van_id | Integer | Van_id from van_comb table |
| Created | Timestamp with time zone | |
| Updated | Timestamp with time zone | |
| Author | integer | |

Suggestions

Every user is encouraged to provide additional decisions and reasons. This table keeps all the suggestions provided by the user.

| NAME | TYPE | COMMENTS |
|---|---|---|
| suggestion_id | Integer | sequence |
| Suggestion_verb | Character varying(100) | |
| Suggestion_noun | Character varying(100) | |
| Suggestion_adjective | Character varying(100) | |
| Suggestion_reasons | Character varying(500)[ ] | |
| Created | Timestamp with time zone | |

User_experience

This table keens all the suggestions for improvement given by the users

| NAME | TYPE | COMMENTS |
|---|---|---|
| ue_id | Integer | sequence |
| Ue_improve | Text | |
| Created | Timestamp with time zone | |

User_questions

This table keeps all yes/no question presented to the user as feedback on using the system. Yes/no values are incremented according to the users' answers.

| NAME | TYPE | COMMENTS |
|---|---|---|
| ueq_id | Integer | sequence |
| Ueq_question | Character varying(200) | |
| Ueq_yes | Integer | |
| Ueq_no | integer | |
| Created | Timestamp with time zone | |
| Updated | Timestamp with time zone | |
| Author | integer | |

Users

This table contains every instance of using the system.

| NAME | TYPE | COMMENTS |
|---|---|---|
| user_id | Integer | sequence |
| User_reason | Character varying(300) | |
| Created | Timestamp with time zone | |
| Van_id | Integer | From van_comb table |
| Reasons | Integer[ ] | From reasons table |
| Fb_reasons | Integer[ ] | from reasons table - show the reasons marked as usefull |
| Demo_ops | Integer[ ] | From demo_options - shows the demo options picked by the user |

Van_comb

This table contains all the associations of verb-noun-adjective

| NAME | TYPE | COMMENTS |
|---|---|---|
| van_id | Integer | sequence |
| Verb_id | Integer | From verbs table |
| noun_id | Integer | From noun table |
| adjective_id | Integer | From adjectives table |
| Visibility | Boolean | Determines if this association will be offered for the users |
| Created | Timestamp with time zone | |
| Updated | Timestamp with time zone | |
| Author | integer | |

Verbs

| NAME | TYPE | COMMENTS |
| --- | --- | --- |
| verb_id | Integer | sequence |
| verb_text | Character varying(100) | |
| Created | Timestamp with time zone | |
| Updated | Timestamp with time zone | |
| Author | integer | |

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

In the description and claims of the application, each of the words "comprise" "include" and "have", and forms thereof, are not necessarily limited to members in a list with which the words may be associated.

What is claimed is:

1. A method for decision reasoning, the method comprising using at least one hardware processor to:
   provide a database comprising decisions, questions and reasons;
   receive, from a user, a selection of a decision being part of said decisions;
   retrieve, from said database, relevant questions out of said questions, wherein said relevant questions are associated, within said database, with said decision received from the user;
   receive, from the user, answers to at least some of said relevant questions;
   process said answers so as to retrieve, from said database, one or more relevant reasons out of said reasons, wherein the one or more relevant reasons are one or more arguments justifying said decision; and
   display said one or more relevant reasons to the user.

2. The method according to claim 1, wherein each of said decisions, questions and reasons is stored in a separate table in said database.

3. The method according to claim 1, wherein each of said decisions is structured based at least on a verb, an adjective and a noun.

4. The method according to claim 1, wherein each of said questions is of a type selected from the group consisting of: a multiple-choice question, a yes/no question and an open-ended question.

5. The method according to claim 1, further comprising using said at least one hardware processor to:
   receive from the user feedback as to said one more relevant reasons; and
   process said feedback so as to adjust an association in said database between at least one of said care or more relevant reasons and said decision selected by the user.

6. The method according to claim 1, further comprising using said at least one hardware processor to receive a suggestion of one or more new decisions from the user, and store said one or more new decisions in the database.

7. The method according to claim 1, further comprising using said at least one hardware processor to receive a suggestion of one or more new reasons from the user, and store said one or more new reasons in the database.

8. A non-transitory computer-readable medium having computer-readable code for decision reasoning stored thereon, that, when executed by at least one hardware processor of a computer, causes the computer to:
   provide a database comprising decisions, questions and reasons;
   receive, from a user, a selection of a decision being part of said decisions;
   retrieve, from said database, relevant questions out of said questions, wherein said relevant questions are associated, within said database, with said decision received from the user;
   receive, from the user, answers to at least some of said relevant questions;
   process said answers so as to retrieve, from said database, one or more relevant reasons out of said reasons, wherein the one or more relevant reasons are one or more arguments justifying said decision; and
   display said one or more relevant reasons to the user.

9. The non-transitory computer-readable medium according to claim 8, wherein each of said decisions, questions and reasons is stored in a separate table in said database.

10. The non-transit computer-readable medium according to claim 8, wherein each of said decisions is structured based at least on a verb, an adjective and a noun.

11. The non-transitory computer-readable medium according to claim 8, wherein each of said questions is of a type selected from the group consisting of: a multiple-choice question, a yes/no question and an open-ended question.

12. The non-transitory computer-readable medium according to claim 8, wherein said computer-readable code, when executed by said at least one hardware processor of the computer, further causes the computer to:
   receive from the user feedback as to said one or more relevant reasons; and
   process said feedback so as to adjust an association in said database between at least one of said one or more relevant reasons and said decision selected by the user.

13. The non-transitory computer-readable medium according to claim 8, wherein said computer-readable code, when executed by said at least one hardware processor of the computer, further causes the computer to receive a suggestion of one or more new decisions from the user, and store said one or more new decisions in the database.

14. The non-transitory computer-readable medium according to claim 8, wherein said computer-readable code, when executed by said at least one hardware processor of the computer, further causes the computer to receive a suggestion of one or more new reasons from the user, and store said one or more ne reasons in the database.

* * * * *